United States Patent [19]

Kameishi

[11] Patent Number: 5,255,667
[45] Date of Patent: Oct. 26, 1993

[54] ENDOSCOPE WITH COMPACT SCOPE END SECTION

[75] Inventor: Wataru Kameishi, Ootawara, Japan
[73] Assignee: Kabushiki Kaisha Toshiba, Kawasaki, Japan
[21] Appl. No.: 758,107
[22] Filed: Sep. 12, 1991
[30] Foreign Application Priority Data
Sep. 12, 1990 [JP] Japan .............. 2-240143
[51] Int. Cl.⁵ .............................. A61B 1/00
[52] U.S. Cl. ............................ 128/4; 128/6
[58] Field of Search ............ 128/6, 4; 358/98
[56] References Cited

U.S. PATENT DOCUMENTS

| | | | |
|---|---|---|---|
| 4,682,219 | 7/1987 | Arakawa | 128/4 X |
| 4,741,327 | 5/1988 | Yabe | 128/6 |
| 4,745,471 | 5/1988 | Takamura et al. | 128/6 X |
| 4,773,396 | 9/1988 | Okazaki | 128/6 |
| 4,809,680 | 3/1989 | Yabe | 128/6 |
| 4,832,003 | 5/1989 | Yabe | 128/6 |
| 4,918,521 | 4/1990 | Yabe et al. | 128/6 X |

Primary Examiner—Richard J. Apley
Assistant Examiner—Karen A. Jalbert
Attorney, Agent, or Firm—Foley & Lardner

[57] ABSTRACT

An endoscope with a compact scope end section structure in which the length of the scope end section in the scope axis direction is shortened. In the endoscope, the scope end section has an optical system for receiving optical image light beam; an imaging element for converting optical image light beams into electric signals; electric components for processing the electric signals obtained by the imaging element, which are located behind sides of the optical system and the imaging element facing away from an end of the scope section; and a flexible substrate permanently affixed to the imaging element at one of the ends and to a processed electrical signal line at its other end for electrically connecting the imaging element and the electric components.

6 Claims, 4 Drawing Sheets

ENDOSCOPE WITH COMPACT SCOPE END SECTION

BACKGROUND OF THE INVENTION

1. Field of the Invention

The present invention relates to an endoscope, and more particularly, to a compact structure for a scope end section of the endoscope.

2. Description of the Background Art

In general, an electronic endoscope apparatus has a scope section shown in FIG. 1, where the scope section comprises a scope end section 1, including an imaging device (not shown), a bending section 2 located adjacent to the scope end section 1, a flexible section 3 connected to the bending section 2 at one end, and an operation section, including an operation knob 5, which is connected with another end of the flexible section 3.

In this scope section of FIG. 1, the bending section 2 is made bendable by manually controlling the operation knob 5 on the operation section 4, so as to be able to adjust the imaging direction of the scope end section 1.

Conventionally, the scope end section 1 has a detailed configuration such as that shown in FIG. 2, for example, where the scope end section 1 includes: an optical system 6 for receiving optical image light beam; a jig member 7 for supporting the optical system 6; an imaging element module 8 for converting the optical image light beam into electric signals, having an imaging surface on which the light beam is focused by the optical system 6; a flexible substrate 9 attached on the imaging element module 8, on which a plurality of electric components 11 such as amplifiers for processing the electric signals obtained by the imaging element module 8 are mounted and connected with the imaging element module 8; and signal lines 10 through which the electric signals obtained by the imaging element module 8 and the electric components 11 are transmitted to a signal processing unit in a system body of an endoscope apparatus.

Alternatively, the conventional scope end section 1 may have a detailed configuration, such as that shown in FIG. 3, where the scope end section 1 has a solid-state imaging element 12 mounted on a glass substrate 16 provided in a frame 17 with electrodes of the solid-state imaging element 12 being electrically connected to electrodes of the glass substrate 16 by a face-down bonding, instead of the imaging element module 8 in the configuration of FIG. 2 described above. A plurality of flexible substrates 9a and 9b having electrodes connected with the electrodes of the glass substrate 16 at one of each of their ends, and with a plurality of signal lines 10a and 10b at their other ends, where an upper flexible substrate 9a is attached on the solid-state imaging element 12 while a plurality of electric components 11 such as amplifiers are mounted on a lower flexible substrate 9b.

In such a conventional configuration for the scope end section 1, the flexible substrate 9 is extended in a scope axis direction, so that the scope end section 1 is inevitably elongated in the scope axis direction according to a number of electric components to be provided on the flexible substrate 9. When this scope end section 1 becomes relatively long in the scope axis direction, the radius for bending the bending section 2 becomes large and this makes the imaging in a narrow portion of a patient difficult and likely to cause pain to the patient.

Moreover, in a conventional configuration for the scope end section 1, only one end of the flexible substrate 9 located close to the scope end is fixedly supported while another end located close to the bending section 2 is left unsupported, so that the flexible substrate 9 is stretched every time the bending section 2 is bent, which in turn causes fatigue, breakage or damage to the flexible substrate 9.

SUMMARY OF THE INVENTION

It is therefore an object of the present invention to provide an endoscope with a compact scope end section structure in which the length of the scope end section in the scope axis direction is shortened.

It is another object of the present invention to provide an endoscope with a tough scope end section structure which can endure the stretching forces exerted by bending, without damage.

According to one aspect of the present invention, there is provided an endoscope having a scope section including a scope end section, the scope end section comprising: an optical system for receiving an optical image light beam; an imaging element for converting the optical image light beam into electric signals; electric components for processing the electric signals obtained by the imaging element; and a flexible substrate through which the imaging element and the electric components are electrically connected, and on which the electric components are mounted, the flexible substrate being curved such that the electric components are located behind a side of the optical system facing away from an end of the scope section.

According to another aspect of the present invention there is provided an endoscope having a scope section including a scope end section, the scope end section comprising: an optical system for receiving an optical image light beam; an imaging element for converting the optical image light beam into electric signals; electric components for processing the electric signals obtained by the imaging element, which are located behind a side of the optical system facing away from an end of the scope section; and a flexible substrate for electrically connecting the imaging element and the electric components.

According to another aspect of the present invention there is provided an endoscope having a scope section including a scope end section, the scope end section comprising: an optical system for receiving optical image light beam; an imaging element for converting the optical image light beam into electric signals; electric components for processing the electric signals obtained by the imaging element, which are located behind sides of the optical system and the imaging element facing away from an end of the scope section; and a flexible substrate for electrically connecting the imaging element and the electric components.

Other features and advantages of the present invention will become apparent from the following description taken in conjunction with the accompanying drawings.

DETAILED DESCRIPTION OF THE PREFERRED EMBODIMENTS

Figure 4:
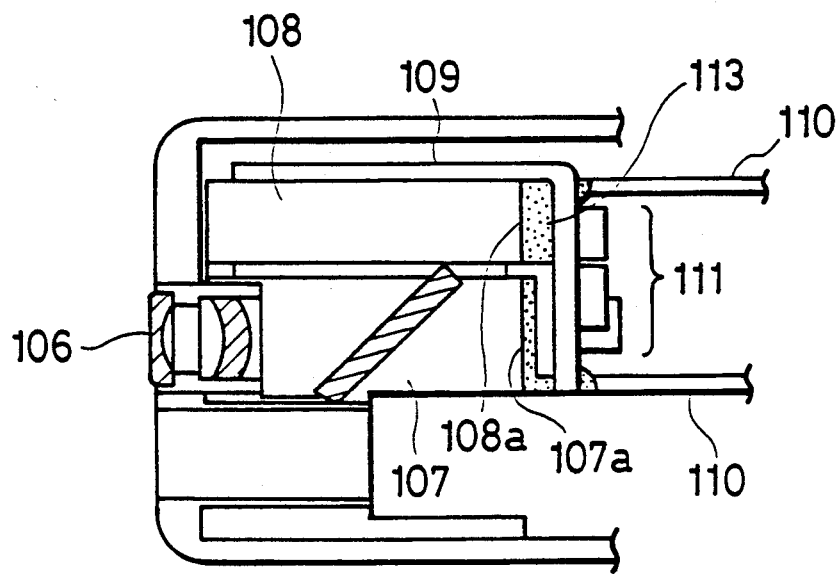
FIG. 4 is a cross sectional view of a first embodiment of a configuration for a scope end section in an endoscope according to the present invention.

Referring now to FIG. 4, a first embodiment of a configuration for a scope end section in an endoscope according to the present invention will be described in detail.

In this first embodiment, the scope end section includes: an optical system 106 for receiving an optical image light beam; a jig member 107 for supporting the optical system 106; an imaging element module for converting the optical image light beam into electric signals, having an imaging surface on which the light beam is focused by the optical system 106; a flexible substrate 109 fixedly attached on the imaging element module 108, on which a plurality of electric components 111, such as amplifiers for processing the electric signals obtained by the imaging element module 108, are mounted and connected with the imaging element module 108; and signal lines 110 through which the electric signals obtained by the imaging element module 108 and the electric components 111 are transmitted to a signal processing unit in a system body of an endoscope apparatus.

Here, the flexible substrate 109 is curved at a corner on a back side 108a of the imaging element module 108 and a curved portion of this flexible substrate 109 is fixedly attached to the back side 108a of the imaging element module 108 and a back side 107a of the jig member 107 by an adhesive material 113, such that the electric components 111 are located behind the imaging element module 108 and the jig member 107, and arranged along a scope diameter direction.

With this configuration, the length of the scope end section in a scope axis direction can be shortened as the electric components 111 are located behind the imaging element module 108 and the jig member 107.

Figure 1:
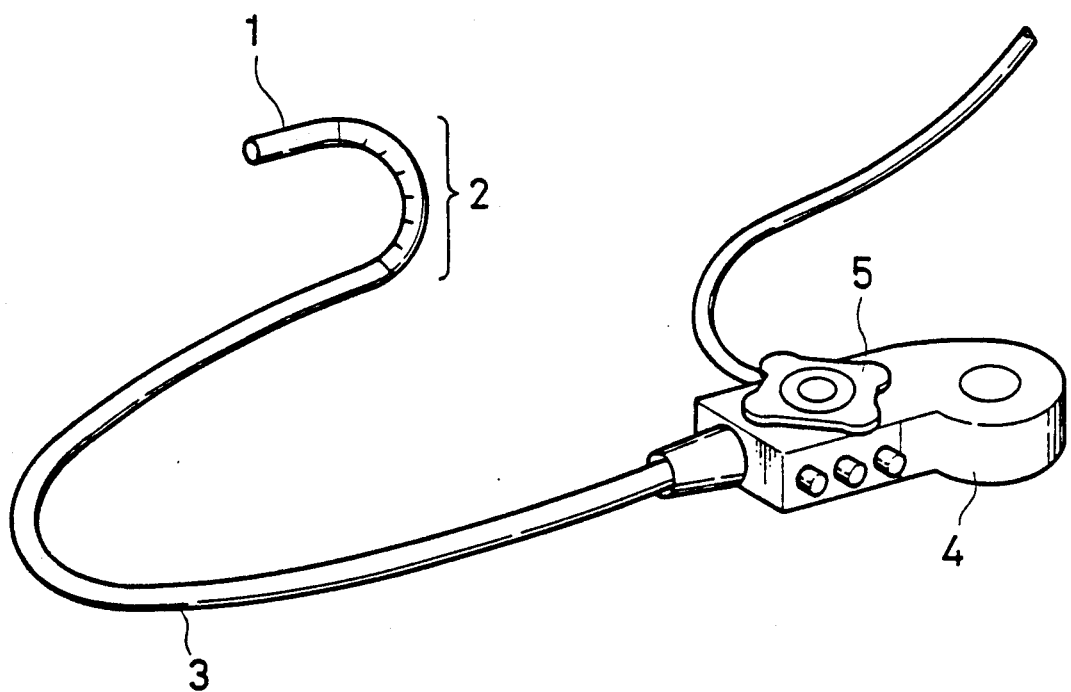
FIG. 1 is a perspective view of a general configuration for a scope section in an endoscope.
Figure 2:
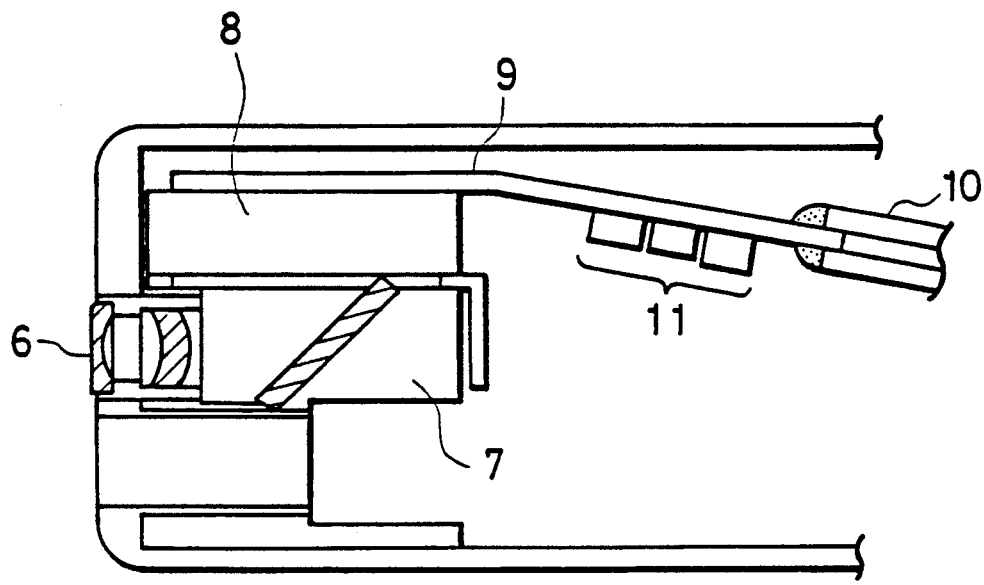
FIG. 2 is a cross sectional view of one example of a conventional configuration for a scope end section in an endoscope.
Figure 3:
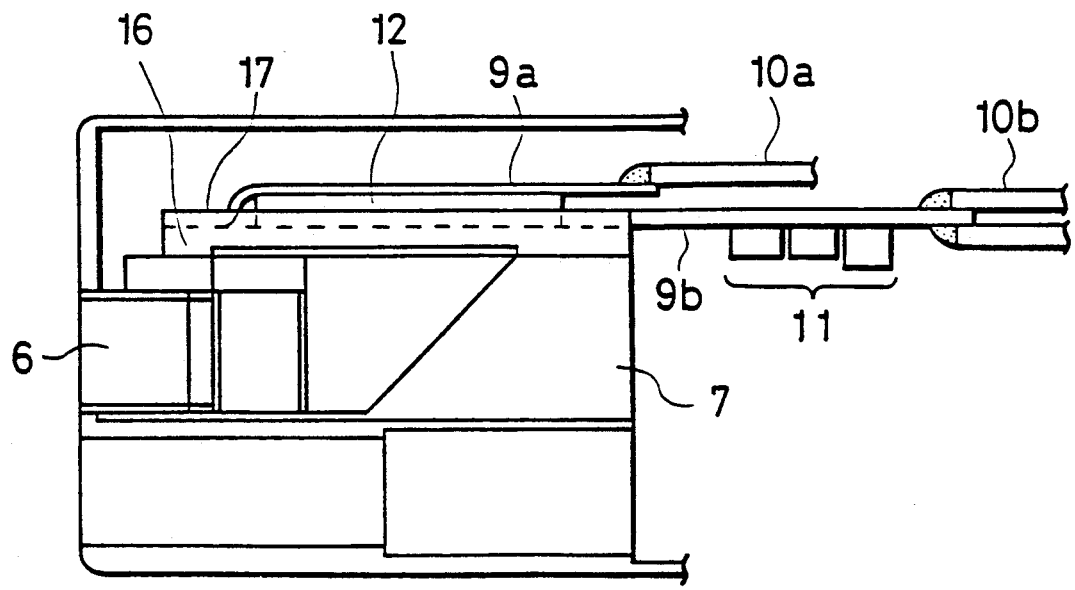
FIG. 3 is a cross sectional view of another example of a conventional configuration for a scope end section in an endoscope.

As a result, the radius for bending the bending section 2 of FIG. 1 can be made small such that the imaging in a narrow portion of a patient becomes possible, and any pain can be reduced.

Moreover, the entire flexible substrate 109 is fixedly attached to the imaging element module 108 and the jig member 107, so that the endurance against the stretching forces exerted by the bending of the bending section 2 can also be improved.

Figure 5:
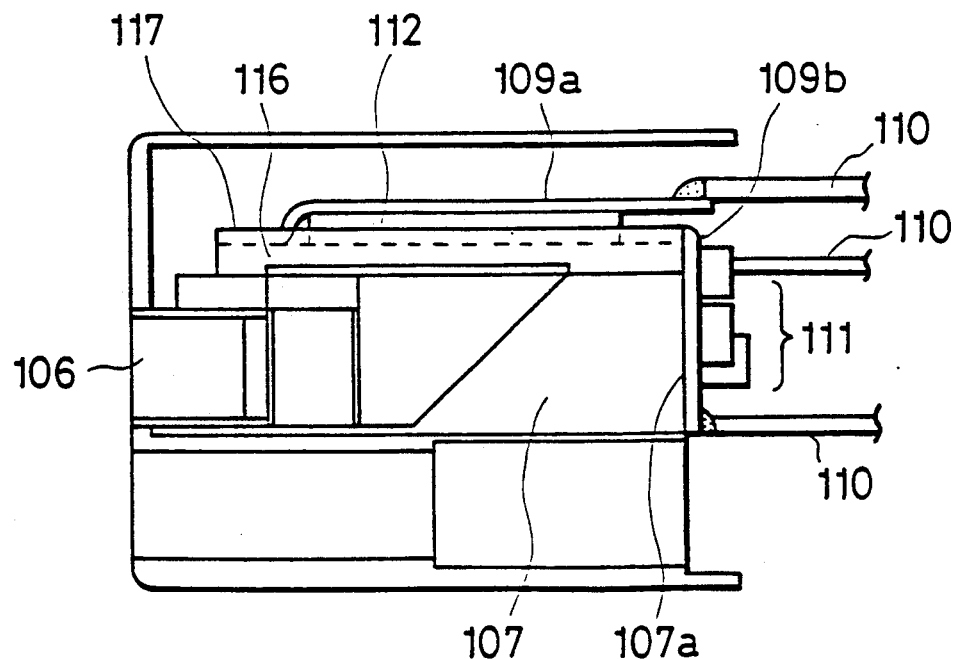
FIG. 5 is a cross sectional view of a second embodiment of a configuration for a scope end section in an endoscope according to the present invention.

Referring now to FIG. 5, a second embodiment of a configuration for a scope end section in an endoscope according to the present invention will be described in detail. Here, the elements equivalent to the corresponding elements in the first embodiment are given the same reference numerals in the figures, and their descriptions are omitted.

In second embodiment, the scope end section has a solid-state imaging element 112 mounted on a glass substrate 116 provided in a frame 117 with electrodes of the solid-state imaging element 112 being electrically connected to electrodes of the glass substrate 116 by a face-down bonding, instead of the imaging element module 108 in the first embodiment described above; and two flexible substrates 109a and 109b having electrodes connected with the electrodes of the glass substrate 116 at one ends and with the signal lines 110 at another ends, where an upper flexible substrate 109a is fixedly attached on the solid-state imaging element 112 while a plurality of electric components 111 such as amplifiers are mounted on a lower flexible substrate 109b.

Here, the lower flexible substrate 109b is curved at a corner on a back side 107a of the jig member 107 and a curved portion of this lower flexible substrate 109b is fixedly attached to the back side 107a of the jig member 107, such that the electric components 111 are located behind the jig member 107, and arranged along a scope diameter direction.

With this configuration, similar to the first embodiment described above, the length of the scope end section in a scope axis direction can be shortened as the electric components 111 are located behind the jig member 107, and the endurance against the stretching forces exerted by the bending of the bending section 2 can also be improved as the flexible substrates 109a and 109b are fixedly attached to the solid-state imaging element 112 and the jig member 107.

Figure 6:
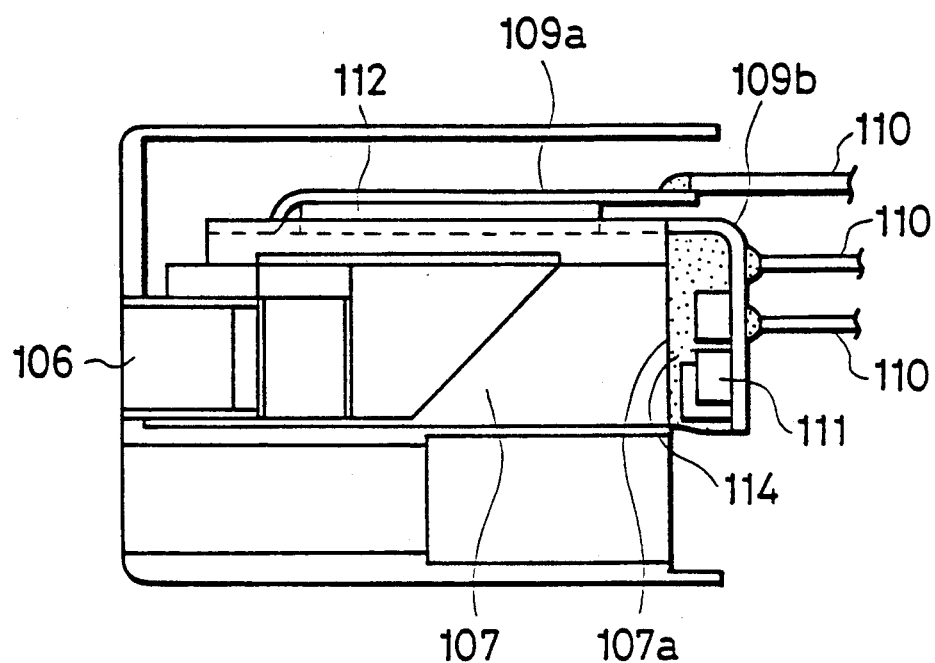
FIG. 6 is a cross sectional view of a third embodiment of a configuration for a scope end section in an endoscope according to the present invention.

Referring now to FIG. 6, a third embodiment of a configuration for a scope end section in an endoscope according to the present invention will be described in detail. Here, those elements which are equivalent to the corresponding elements in the first and second embodiments described above will be given the same reference numerals in the figures and their descriptions are omitted.

In this third embodiment, the scope end section has a configuration similar to that of the second embodiment described above, except that the curved portion of the lower flexible substrate 109b is spaced from the back side 107a of the jig member 107 such that the electric components 111 mounted on the lower flexible substrate 109b are located in a clearance formed between the back side 107a of the jig member 107 and the curved portion of the lower flexible substrate 109b, where this clearance is filled with filler material 114.

With this configuration, similarly to the second embodiment described above, the length of the scope end section in a scope axis direction can be shortened as the electric components 111 are located behind the jig member 107.

In addition, the electric components 111 are located in the clearance filled with the filler material 114, there is no danger for the electric components 111 to be damaged by accidental contacts with other parts of the scope end section, so that the reliability and lifetime of the electric components 111 can be improved.

Figure 7:
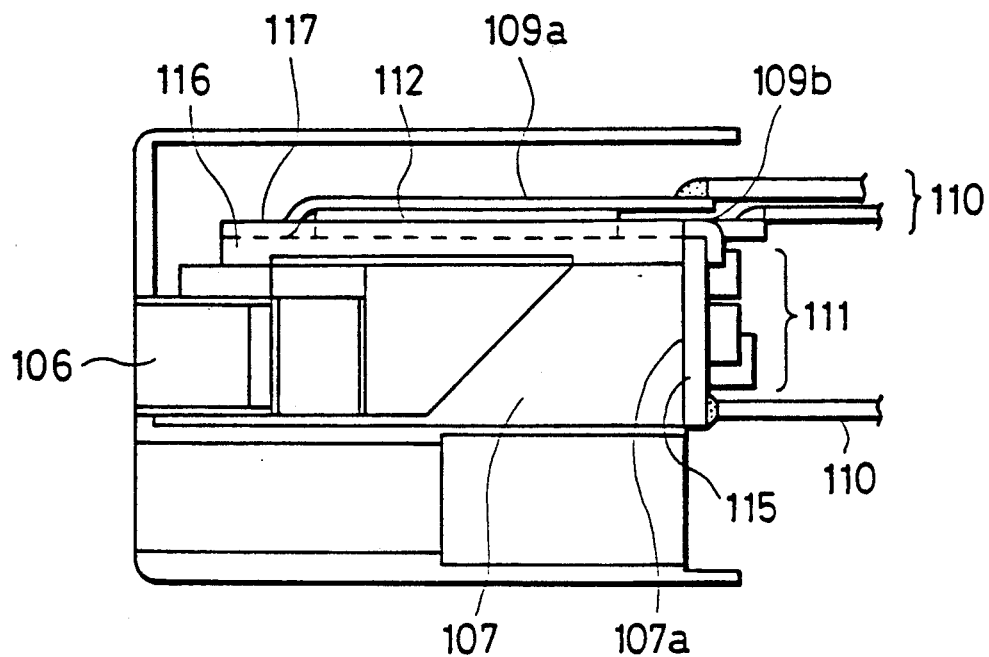
FIG. 7 is a cross sectional view of a fourth embodiment of a configuration for a scope end section in an endoscope according to the present invention.

Referring now to FIG. 7, a fourth embodiment of a configuration for a scope end section in an endoscope according to the present invention will be described in detail. Here, those elements which are equivalent to the corresponding elements in the first and second embodiments described above will be given the same reference numerals in the figures and their descriptions are omitted.

In this fourth embodiment, the scope end section has a configuration similar to that of the second embodiment described above, except that the electric components 111 are mounted on an additional substrate 115 fixedly attached on the back side 107a of the jig member 107, and the lower flexible substrate 109b is electrically connected with this additional substrate 115 at a corner of the additional substrate 115.

With this configuration, similarly to the second and embodiment described above, the length of the scope end section in a scope axis direction can be shortened as the electric components 111 are located behind the jig member 107, and the endurance against the stretching forces exerted by the bending of the bending section 2 can also be improved as the flexible substrates 109a and 109b and the additional substrate 115 are fixedly attached to the solid-state imaging element 112 and the jig member 107.

It is to be noted that the first to fourth embodiments described above may be combined in various manners to obtain a modified configuration.

Besides these, many modifications and variations of the above embodiments may be made without departing from the novel and advantageous features of the present invention. Accordingly, all such modifications and variations are intended to be included within the scope of the appended claims.

What is claimed is:

1. An endoscope having a scope section including a scope end section, the scope end section comprising:
   an optical system for receiving optical image light beams;
   an imaging element for converting the optical image light beams into electric signals;
   electric components for processing the electric signals obtained by the imaging element; and
   a flexible substrate through which the imaging element and the electric components are electrically connected, and on which the electric components are mounted, the flexible substrate being curved such that the electric components are located behind a side of the optical system facing away from an end of the scope section, the flexible substrate being fixedly attached to and mounted on said side of the optical system facing away from the end of the scope section.

2. The endoscope of claim 1, wherein the electric components are arranged along a scope diameter direction.

3. An endoscope having a scope section including a scope end section, the scope end section comprising:
   an optical system for receiving optical image light beams;
   an imaging element for converting the optical image light beam into electric signals;
   electric components for processing the electric signals obtained by the imaging element, which are located behind a side of the optical system facing away from an end of the scope section;
   a flexible substrate for electrically connecting the imaging element and the electric components; and
   an additional flexible substrate fixedly attached to and mounted on said side of the optical system facing away from the end of the scope section, on which the electric components are mounted and to which the flexible substrate is electrically connected.

4. The endoscope of claim 3, wherein the electric components are arranged along a scope diameter direction.

5. An endoscope having a scope section including a scope end section, the scope end section comprising:
   an optical system for receiving optical image light beams;
   an imaging element for converting the optical image light beams into electric signals;
   electric components for processing the electric signals obtained by the imaging element, which are located behind sides of the optical system and the imaging element facing away from an end of the scope section;
   a flexible substrate for electrically connecting the imaging element and the electric components; and
   an additional flexible substrate fixedly attached to and mounted on said sides of the optical system and imaging element facing away from the end of the scope section, on which the electric components are mounted and to which the flexible substrate is electrically connected.

6. The endoscope of claim 5, wherein the electric components are arranged along a scope diameter direction.

* * * * *